United States Patent [19]

Wu et al.

[11] Patent Number: 5,691,333
[45] Date of Patent: Nov. 25, 1997

[54] PESTICIDAL 1-ARYLPYRAZOLE-3-CARBOXIMIDOTHOIC ACID ESTERS

[75] Inventors: Tai-Teh Wu, Chapel Hill; Michael Thomas Pilato, Cary, both of N.C.

[73] Assignee: Rhone-Poulenc Inc., Research Triangle Park, N.C.

[21] Appl. No.: 796,107

[22] Filed: Feb. 6, 1997

Related U.S. Application Data

[62] Division of Ser. No. 593,904, Jan. 30, 1996, Pat. No. 5,629,335, which is a continuation of Ser. No. 418,681, Apr. 7, 1995, abandoned.

[51] Int. Cl.$^6$ .......................... A01N 43/78; A01N 43/86; C07D 417/04
[52] U.S. Cl. .................. 514/226.5; 514/365; 544/55; 548/146
[58] Field of Search .......................... 544/55; 548/146; 514/226.8, 365

[56] References Cited

U.S. PATENT DOCUMENTS

| | | |
|---|---|---|
| 4,614,534 | 9/1986 | Stetter et al. .............................. 548/146 |
| 4,918,085 | 4/1990 | D'Silva et al. .. |
| 4,931,461 | 6/1990 | Jensen-Korte et al. .. |
| 4,963,575 | 10/1990 | Buntain et al. .. |
| 5,047,550 | 9/1991 | D'Silva et al. .. |
| 5,079,370 | 1/1992 | D'Silva et al. .. |
| 5,104,994 | 4/1992 | Roberts et al. .. |
| 5,177,100 | 1/1993 | Roberts et al. .. |
| 5,232,940 | 8/1993 | Hatton et al. .. |
| 5,306,694 | 4/1994 | Phillips et al. .. |

FOREIGN PATENT DOCUMENTS

| | | |
|---|---|---|
| 0234119 | 9/1987 | European Pat. Off. . |
| 0295117 | 12/1988 | European Pat. Off. . |
| 0352944 | 1/1990 | European Pat. Off. . |
| 0403300 | 12/1990 | European Pat. Off. . |
| 0403309 | 12/1990 | European Pat. Off. . |
| 0500209 | 8/1992 | European Pat. Off. . |
| 87/03781 | 7/1987 | WIPO . |
| 93/06089 | 4/1993 | WIPO . |
| 94/21606 | 9/1994 | WIPO . |

*Primary Examiner*—Robert W. Ramsuer
*Attorney, Agent, or Firm*—Burns, Doane, Swecker & Mathis, L.L.P.

[57] ABSTRACT

1-(Substituted phenyl)-3-(thioimidate)pyrazoles having systemic activity, arthropodicidal (especially insecticidal) and nematocidal compositions comprising same and methods for controlling arthropods (especially insects) and nematodes.

29 Claims, No Drawings

PESTICIDAL 1-ARYLPYRAZOLE-3-CARBOXIMIDOTHOIC ACID ESTERS

This application is a divisional of application Ser. No. 08/593,904, filed Jan. 30, 1996, now U.S. Pat. No. 5,629,335 which is a continuation of application Ser. No. 08/418,681, filed Apr. 7, 1995 abandoned.

BACKGROUND OF THE INVENTION

1. Field of the Invention

The invention relates to new 3-(sulfur containing substituent) derivatives of 1-arylpyrazoles and related compounds. The invention further pertains to compositions of said compounds and methods, using said compounds, for the control of arthropod or nematode pests, in particular to the application of said compounds or compositions in agricultural methods of use, particularly as pesticides, for controlling arthropods, especially insects by systemic action.

2. Description of the Related Art

International Patent Publication No. WO 87/03781 and European Patent Publication No. 0295117 describe insecticidal 1-(substituted phenyl) pyrazoles.

International Patent Publications No. WO 93/06089 and WO 94/21606 also describe insecticidal 1-(4-$SF_5$ substituted phenyl) heterocycles which may be pyrroles as well as imidazoles or pyrazoles. The teaching of these patents is not substantially different from that of International Patent Publication No. WO 87/03781 or from that of European Patent Publication No. 0295117 as far as pyrazoles are concerned.

OBJECTS AND SUMMARY OF THE INVENTION

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, or plant nematodes, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, miticidal, foliar insecticidal, soil insecticidal and nematocidal, systemic, antifeeding or pesticidal activity via seed treatment.

A fourth object of the present invention is to provide compounds with substantially enhanced and more rapid activity, especially against insects and more particularly insects in their larval stages.

A fifth object of the present invention is to provide compounds with greatly improved (faster and greater) penetration into pest species when topically applied and to thus provide enhanced movement of the compounds to the pesticidal site(s) of action within the pest.

Another object of the present invention is to provide compounds with high activity and improved safety to the user and the environment, which are obtained by optimization of chemical, physical and biological properties such as solubility, melting point, stability, electronic and steric parameters, and the like.

These and other objects of the invention shall become readily apparent from the description of the present invention which follows.

This invention embraces novel chemical compounds having an insecticidal, miticidal or nematocidal activity, with an improved systemic activity over the closest compounds.

The invention thus relates to compounds having the formula:

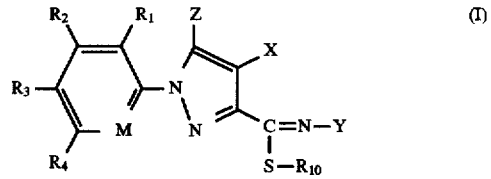

and the agriculturally acceptable salts, especially the halohydrates, thereof, wherein:

$R_1$ is H or halogen;

$R_2$ is H, halogen or lower alkyl;

$R_3$ is halogen, haloalkyl, haloalkoxy, $R_{16}S(O)_n$ or $SF_5$; preferably, $R_3$ is halogen, haloalkyl or haloalkoxy;

$R_4$ is H, halogen or lower alkyl;

X is $R_6$ or, preferably, —$S(O)_n$—$R_5$;

n is 0, 1 or 2;

$R_5$ is a lower hydrocarbyl or halohydrocarbyl radical which is saturated or is ethylenically or acetylenically unsaturated, such as the radicals alkyl, haloalkyl, alkenyl, haloalkenyl, alkynyl and haloalkynyl; or a $C_3$-$C_5$ cycloalkyl radical; preferably, $R_5$ is alkyl;

$R_6$ is one of the meanings given for $R_5$, or $R_6$ is thiocyanato, nitro, cyano or halogen;

Z is hydrogen; halogen; a lower alkyl radical which is unsubstituted or is substituted by one or more substituents chosen from halogen, hydroxy, alkoxy, alkenyl and cyano; $R_{14}S(O)_n$; $R_{16}S(O)_n$ alkyl; amino; $R_{15}CO$— in which $R_{15}$ is H or an alkyl radical which is unsubstituted or is substituted by one or more halogen, hydroxy or alkoxy; cyano; nitro; trialkylsilyl; trialkylsilylmethyl; alkoxycarbonyl; alkylthiocarbonyl; hydrazino; —CH=NOH; —CH=NO—alkyl; $C_2$-$C_4$ alkenyl; $C_2$-$C_4$ alkynyl; alkoxy; alkylcarbonylthio; alkoxycarbonylthio; aroylthio; aryl—$S(O)_n$; azido; arylalkyl—$S(O)_n$; 1H-pyrrol-1-yl; 1H-pyrazol-1-yl; $R_7$NH—; or $R_8R_9N$—;

each of $R_7$, $R_8$ and $R_9$, which are identical or different, is lower alkyl, lower alkyl—$S(O)_n$, $P(=O)(R_5)(OR_5)$, aroyl, aryloxycarbonyl, formyl, alkenyl, alkynyl, alkoxycarbonyl, alkylthiocarbonyl or alkylcarbonyl, the alkyl portion of which radicals is optionally substituted by one or more $R_{17}$;

or $R_8$ and $R_9$ are joined so as together to form a divalent radical having 4 to 6 atoms in the chain, this divalent radical being alkylene, alkyleneoxyalkylene or alkyleneaminoalkylene;

Y is hydrogen or $C_3$-$C_7$ cycloalkyl; or Y is an alkyl, alkenyl, alkynyl, arylakyl, aroyl, alkoxycarbonyl, alkylcarbonyl or arylalkylcarbonyl radical which is optionally substituted by one or more $R_{18}$;

$R_{10}$ is alkenyl, haloalkenyl, alkynyl or haloalkynyl, or alkyl optionally substituted by one or more $R_{19}$; or $R_{10}$ is aralkyl, aryl, pyridinyl, pyrimidinyl, trialkylsilyl or $C_3$-$C_7$ cycloalkyl;

or the groups S—$R_{10}$ and N—Y are joined together, with the —C= group to which they are attached, to form a heterocyclic ring having 5 to 8 ring atoms;

$R_{14}$ is lower alkyl, lower alkenyl or lower alkynyl, each of which is optionally substituted with one or more halogen;

$R_{16}$ is lower alkyl or lower haloalkyl;

$R_{17}$ is hydrogen, nitro, cyano, alkoxy, haloalkoxy, $R_{16}S(O)_n$, alkylcarbonyl, alkoxycarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl;

$R_{18}$ is halogen, alkoxy, cyano, alkyl—$S(O)_n$ or arylthio;

$R_{19}$ is alkoxy, alkoxycarbonyl, cyano, aminocarbonyl, hydroxycarbonyl, alkylaminocarbonyl, dialkylaminocarbonyl, alkylamino, dialkylamino, amino, halogen, alkyl—$S(O)_n$, $NO_2$, alkylcarbonyl, hydroxy, acylamino or acyloxy; and M is C—halo, C—CN, C—$CH_3$, C—$CH_2F$, C—$NO_2$, C—$CH_2Cl$ or N, provided that when $R_1$ is halogen, then M can also be CH.

The halohydrate derivatives are especially considered for the compounds wherein Y is H.

DETAILED DESCRIPTION OF THE INVENTION

In the instant invention, some words are used in a specific sense:

The term "$R_{14}S(O)_n$" means a radical of the formula —$S(O)_nR_{14}$. The term "$R_{16}S(O)_n$alkyl" means a radical of the formula —alkylene—$S(O)_nR_{16}$. The term "alkylthiocarbonyl" means a radical of the formula

The term "alkylcarbonylthio" means an alkanoylthio radical, i.e. a radical of the formula

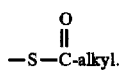

The term "alkoxycarbonylthio" means a radical of the formula

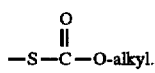

The term "aroylthio" means a radical of the formula

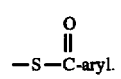

The term "arylalkyl" means an aralkyl radical, i.e. a radical of the formula —alkylene—aryl. Similarly, the term "arylalkyl—$S(O)_n$" means an —$S(O)_n$—aralkyl radical, that is, a radical of the formula —$S(O)_n$—alkylene—aryl; and the term "arylalkylcarbonyl" means an aralkanoyl radical, i.e. a radical of the formula

The term "alkylcarbonyl" means an alkanoyl radical, that is, a radical of the formula

The term "alkyl—$S(O)_n$" means a radical of the formula —$S(O)_n$—alkyl. The term "$R_{16}S(O)_n$" means a radical of the formula —$S(O)_nR_{16}$.

The term "aminocarbonyl" means a carbamoyl radical, that is, a radical of the formula

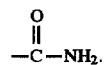

Similarly, the term "alkylaminocarbonyl" means an alkylcarbamoyl radical, that is, a radical of the formula

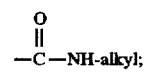

and the term "dialkylaminocarbonyl" means a dialkylcarbamoyl radical, that is, a radical of the formula

in which the alkyl moieties can be the same or different. Analogously, the term "dialkylamino" means a radical of the formula —$N(alkyl)_2$ in which the alkyl moieties can be the same or different.

The term "hydroxycarbonyl" means a carboxyl radical, that is, —COOH. The term "aminosulfonyl" means a sulfamoyl radical, that is, —$SO_2NH_2$. Similarly, the term "alkylaminosulfonyl" means an alkylsulfamoyl radical, that is, a radical of the formula —$SO_2NH$—alkyl; while the term "dialkylaminosulfonyl" means a dialkylsulfamoyl radical, which has the formula —$SO_2N(alkyl)_2$ wherein the alkyl moieties can be the same or different.

The term "alkylcarbonylalkyl" means (alkanoyl)alkyl, i.e. a radical of the formula

The term "aminocarbonylalkyl" means (carbamoyl)alkyl, i.e. a radical of the formula

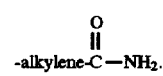

Similarly, the term "alkylaminocarbonylalkyl" designates an (alkylcarbamoyl)alkyl radical, that is, a radical of the formula

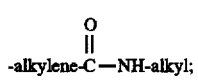

and the term "dialkylaminocarbonylalkyl" means a (dialkylcarbamoyl)alkyl radical, that is, a radical of the formula

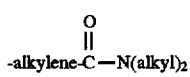

-alkylene-C(=O)—N(alkyl)$_2$ in which the alkyl moieties can be the same or different.

The term "halo" before the name of a radical means that this radical is partially or completely halogenated, that is to say, substituted by F, Cl, Br or I, in any combination, preferably by F or Cl. The term "halogen" means F, Cl, Br or I. The term lower before the name of a radical having a carbon skeleton means that this carbon skeleton has less than 6 carbon atoms. When the name of any substituent is repeated, it keeps the same meaning unless otherwise specified. The term "aryl" designates an aromatic radical which is preferably phenyl, optionally substituted with one or more substituents selected from halogen, methyl and methoxy, especially phenyl, halophenyl, tolyl or xylyl. The term "aroyl" designates a carbonyl-aromatic radical, that is,

aryl-C(=O)—, which is preferably a benzoyl, methylbenzoyl, halobenzoyl or xylylcarbonyl radical. The term "acyl" designates an alkylcarbonyl radical. The term "acylamino" similarly designates an alkylcarbonylamino radical, also referred to as an alkanoylamino radical, which has the formula

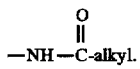

—NH—C(=O)—alkyl.

In like fashion, the term "acyloxy" means an alkylcarbonyloxy radical, that is, an alkanoyloxy radical, which has the formula

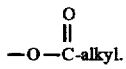

—O—C(=O)—alkyl.

The various individual radicals (like alkyl, alkenyl, alkynyl, alkoxy and alkylene, or the like) are generally and preferably lower radicals.

When Z represents a ring system, it is preferably 1H-pyrrol-1-yl, 1H-pyrazol-1-yl, morpholinyl, pyrrolidinyl, piperidinyl, piperazinyl or hexamethyleneimino.

Particularly preferred compounds of the above formula (I) are those having the formula:

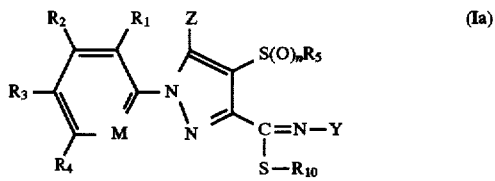

(Ia)

wherein:

M is CH, CCl, CF, CBr or N;

$R_1$ is F, Cl, Br or H, provided that $R_1$ is other than H when M is CH;

$R_2$ and $R_4$ are H;

$R_3$ is —CF$_3$, —OCF$_3$, —CHF$_2$, —S(O)$_n$CF$_3$, —CF$_2$Cl, —CFCl$_2$, —OCF$_2$Cl, —OCFCl$_2$, Cl, Br or F;

Z is H, halogen (F, Cl, Br), C$_1$-C$_3$ alkyl, C$_1$-C$_3$ haloalkyl, C$_2$-C$_3$ alkenyl, alkoxy, alkylthio, alkylsulfinyl, alkylsulfonyl, azido, amino, —NHR$_{11}$ or —NR$_{12}$R$_{13}$, wherein each of R$_{11}$, R$_{12}$ and R$_{13}$, which are identical or different, is C$_1$-C$_3$ alkyl, C$_2$-C$_3$ alkenyl, C$_1$-C$_5$ alkylcarbonyl or C$_1$-C$_5$ alkoxycarbonyl, in which the alkyl, alkenyl, alkylcarbonyl and alkoxycarbonyl groups are unsubstituted or are substituted with cyano, alkoxy, alkyl—S(O)$_n$, nitro, alkoxycarbonyl, alkylcarbonyl, aminocarbonyl, alkylaminocarbonyl, dialkylaminocarbonyl, hydroxycarbonyl, hydroxy or halogen (F, Cl, Br);

Y is hydrogen, C$_1$–C$_6$ alkyl, C$_2$–C$_6$ alkenyl, C$_2$–C$_6$ alkynyl, alkylcarbonyl, arylcarbonyl, arylalkyl, alkoxycarbonyl, alkoxyalkyl or alpha-alkoxyarylalkyl;

R$_{10}$ is C$_1$–C$_6$ alkyl, C$_2$–C$_6$ alkenyl, C$_2$–C$_6$ alkynyl, cyanoalkyl, alkoxycarbonylalkyl, aryl, carboxyalkyl, alkylcarbonylalkyl, aminocarbonylalkyl, alkylaminocarbonylalkyl, dialkylaminocarbonylalkyl or R$_{16}$S(O)$_n$alkyl—;

or the groups S—R$_{10}$ and N—Y are joined together, with the —C= group to which they are attached, to form a heterocyclic ring having 5 or 6 ring atoms;

and R$_5$, R$_{16}$ and n are as defined with formula (I) above.

For the above preferred compounds, there are optimum combinations of substituent groups.

Preferred phenyl groups or pyridyl groups comprising the R$_1$-R$_4$ and M radicals in formula (I) or (Ia) are: 2,6-dichloro-4-trifluoromethylphenyl; 2,6-dichloro-4-trifluoromethoxyphenyl; 2-bromo-6-chloro-4-trifluoromethylphenyl; 2-bromo-6-chloro-4-trifluoromethoxyphenyl; 2,6-difluoro-4-trifluoromethylphenyl; 2-chloro-4-trifluoromethylphenyl; 2,6-dichloro-3-methyl-4-trifluoromethylphenyl; 3-chloro-5-trifluoromethyl-2-pyridinyl; 3-chloro-5-trifluoromethoxy-2-pyridinyl; 3,5-dichloro-2-pyridinyl; 2,6-dichloro-4-bromophenyl; 2,4,6-trichlorophenyl; 2-bromo-6-fluoro-4-difluoromethylphenyl; 2-chloro-6-fluoro-4-trifluoromethylphenyl; 2,6-dibromo-4-trifluoromethylphenyl; 2,6-dibromo4-trifluoromethoxyphenyl; and 2-bromo-4-trifluoromethylphenyl.

Further preferred compounds of formula (I) or (Ia) are those wherein the Z substituent is: hydrogen; acetylamino; amino; 2-n-butoxypropionylamino; methyl; hydroxyacetylamino; ethyl; 3-ethylsulfinylpropylamino; bromo; acetyl; formylamino; chloro; methylamino; vinyl; ethylamino; 2-hydroxyethylamino; 2-methoxyethylamino; methylsulfonylamino; 2-ethylsulfonylethylamino; 4-methoxybenzoylamino; 2-cyanoethylamino; 4-methoxybenzylamino; 2-methylthioethylamino; 2-aminocarbonylethylamino (2-carbamoylethylamino); 2-methylsulfinylethylamino; 3-methoxycarbonylpropylamino; 2-ethylsulfonylethylamino; 2-methylsulfonylethylamino; cyanomethylamino; 2-ethylthioethylamino; aminocarbonylmethylamino (carbamoylethylamino); dimethylamino; 2-nitroethylamino; 2-acetylethylamino; or methylcarbonylmethylamino (acetylmethylamino).

Further preferred compounds of formula (I) or (Ia) are those wherein —S(O)$_n$R$_5$ is: methylthio; bromodifluoromethylsulfinyl; methylsulfinyl; bromodifluoromethylsulfonyl; methylsulfonyl; difluoromethylthio; trifluoromethylthio; difluoromethylsulfinyl; trifluoromethylsulfinyl; difluoromethylsulfonyl; trifluoromethylsulfonyl; chlorofluoromethylthio; ethylsulfinyl; chlorofluoromethylsulfinyl; ethylsulfonyl; chlorofluoromethylsulfonyl; chlorodifluoromethylthio; bromochlorofluoromethylthio; chlorodifluoromethylsulfinyl; bromochlorofluoromethylsulfinyl; chlorodifluoromethylsulfonyl; bromochlorofluoromethylsulfonyl; dichlorofluoromethylthio; pentafluoroethylthio; dichlorofluoromethylsulfinyl; pentafluoroethylsulfinyl; dichlorofluoromethylsulfonyl; pentafluoroethylsulfonyl; bromodifluoromethylthio; ethylthio; vinylthio; vinylsulfinyl; cyclopropylthio; cyclopropylsulfinyl; cyclopropylsulfonyl; isopropylsulfinyl; isopropylsulfonyl; or isopropylthio.

Further preferred compounds of formula (I) and (Ia) are those wherein $R_{10}$ is: methyl; ethyl; isopropyl; allyl; 2-methylallyl; propargyl; 2-cyanoethyl; 2-cyano-2-methylethyl; 2-ethoxycarbonylethyl; 2-methoxycarbonylethyl; phenyl; 3-chlorophenyl; 4-chlorobenzyl; or carboxymethyl.

Further preferred compounds of formula (I) and (Ia) are those wherein the Y substituent is: hydrogen; methoxycarbonyl; methyl; ethoxycarbonyl; ethyl; allyl; propargyl; acetyl; 1-methoxyethyl; or benzyl.

Further preferred compounds of formula (I) and (Ia) are those wherein —S—$R_{10}$ and Y—N=C— are joined together into the divalent radical —S—$CH_2CH_2$—N=C— or —S—$CH_2CH_2CH_2$—N=C—.

Method or Processes of Synthesis

1) From 1-Arylpyrazole-3-carbonitriles

The compounds of formula (I) can be prepared directly from 1-arylpyrazole-3-carbonitriles (A) and/or (B) by treatment with a thiol ($R_{10}$—SH) in the presence of anhydrous HCl, followed by contact of the resulting hydrochloride salt with a base, as described in Annalen der Chemie, 197, 348, 350 (1897), according to the scheme:

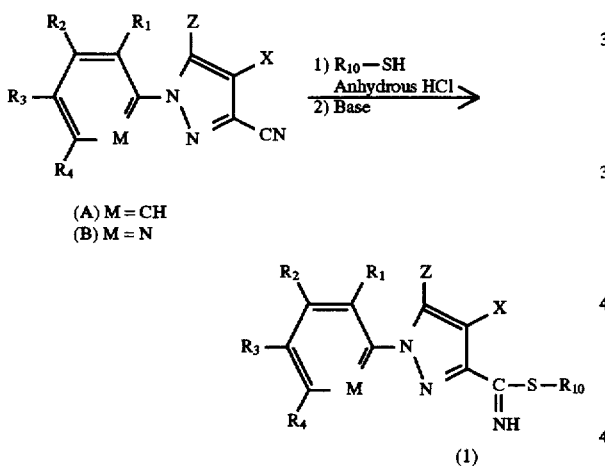

Frequently, the hydrochloride salts of the resulting thioimidates can be isolated and, as desired, converted to the free R'—C($SR_{10}$)=NH compounds by treatment with a base. An equivalent of anhydrous hydrogen chloride is most generally used as the condensing agent and is preferred; the other hydrogen halides can also be used. The thiols and nitriles react in equivalent mounts but ratios of reactants are not critical and may range from approximately 100:1 in either direction. It is generally preferred, however, to use an excess of the relatively inexpensive thiol ($R_{10}$—SH) to ensure complete conversion of the more costly nitrile.

Ethyl ether is the solvent most frequently employed in this reaction, but diisopropyl ether, methyl tert-butyl ether, dioxane, tetrahydrofuran or other ethers can be used. Other suitable solvents include benzene, toluene, dichloromethane, carbon tetrachloride, chloroform, ligroin, hexane, cyclohexane and mixtures of the above.

A reaction temperature of from about 0° C. to about 5° C., employing an ice/water bath, is preferred, but reaction temperatures of from approximately −50° C. to about 30° C. are operable and the freezing point of the solvent may limit the minimum temperature. Pressure conditions of the reaction are not critical; however, operation at atmospheric pressure is most convenient.

Thioimidates are sensitive to solvolytic conditions and their liberation from their salts requires some care. A cold, aqueous carbonate [J. Chem. Soc., 1791 (1955)] or bicarbonate [J. Chem. Soc., 3220 (1949)] (potassium, sodium salts, etc.) solution is the method of choice. A non-protic base such as a trialkylamine (for example, triethylamine) or pyridine, or a sterically hindered alkoxide such as a tertiary alkoxide (for example, potassium tert-butoxide) can also be employed.

The starting 1-phenylpyrazole-3-carbonitrile intermediates of formula (A) are known or can be prepared by methods or processes as described in EP 0295117 and EP 0234119 and WO 87/03781, all of which are incorporated herein by reference and relied upon.

In a manner analogous to the preparation of the 1-phenylpyrazole-3-carbonitrile intermediates, the starting 1-(2-pyridinyl)pyrazole-3-carbonitrile intermediates of formula (B) are known or can be prepared by methods or processes as described in EP 0500209, also incorporated herein by reference.

2) From 1-Arylpyrazole-3-thiocarboxamides

Thioamides (2) react with various alkylating agents ($R_{10}$-leaving moiety) to afford thioimidate salts, yielding the free thioimidates (1) on treatment with a base, according to the scheme:

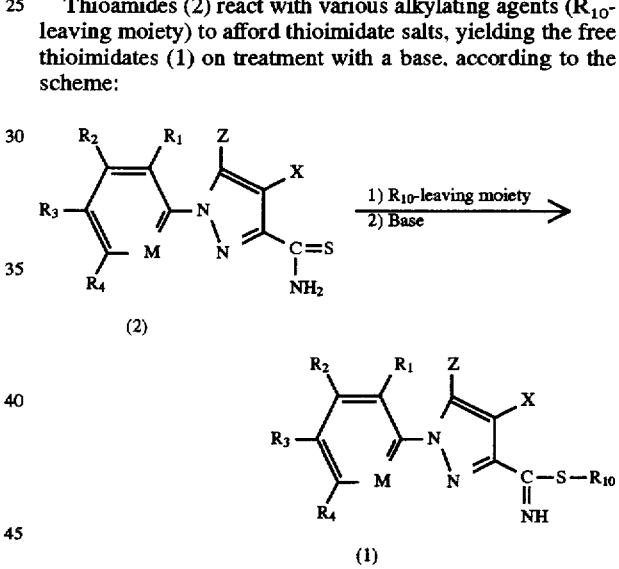

Thus, in J. Chem. Soc., 3220 (1949), a thioamide was treated with an excess of methyl iodide in dry $CHCl_3$, resulting in an S-methyl thioimidate salt —C($SCH_3$)=NH HI. Conversion of a thioimidate salt to a free thioimidate can be conducted by contact with an aqueous base such as cold, aqueous $K_2CO_3$ [J. Chem. Soc., 1791 (1955)].

It is more convenient, however, to convert the thioamides (2) to thioimidate esters (1) in one step, by combined treatment of (2) with an alkylating agent ($R_{10}$-leaving moiety) and base; this is the preferred method. The molar ratio of $R_{10}$-leaving moiety to thioamide is not critical and can range from approximately 100 to one in either direction. It is preferred, however, to employ an excess of the $R_{10}$-leaving moiety agent to effect complete conversion of the more expensive thioamide precursor. The amount of base employed should be sufficient to neutralize all by-product hydrogen halide (H-halogen).

As alkylating agents ($R_{10}$-leaving moiety), one can employ alkyl halides, such as methyl iodide, ethyl bromide or butyl chloride, or dialkyl sulfates, such as dimethyl sulfate or diisopropyl sulfate. For the alkylation reaction, useful solvents include tetrahydrofuran, dioxane, ethyl ether, nitromethane or benzene. The use of a metal complexing agent, such as a crown ether, may be of benefit in accelerating the reaction.

The alkylation reactions are preferably run at about room temperature. Allowable temperatures, however, can range from about −20° C. to about 50° C. Pressure conditions are not critical and operation at atmospheric pressure is preferred.

3) Preparation of N,S-Disubstituted Derivatives (4)

The N,S-disubstituted compounds (4) are made by the following two-step sequence, providing selective substitution on N and S:

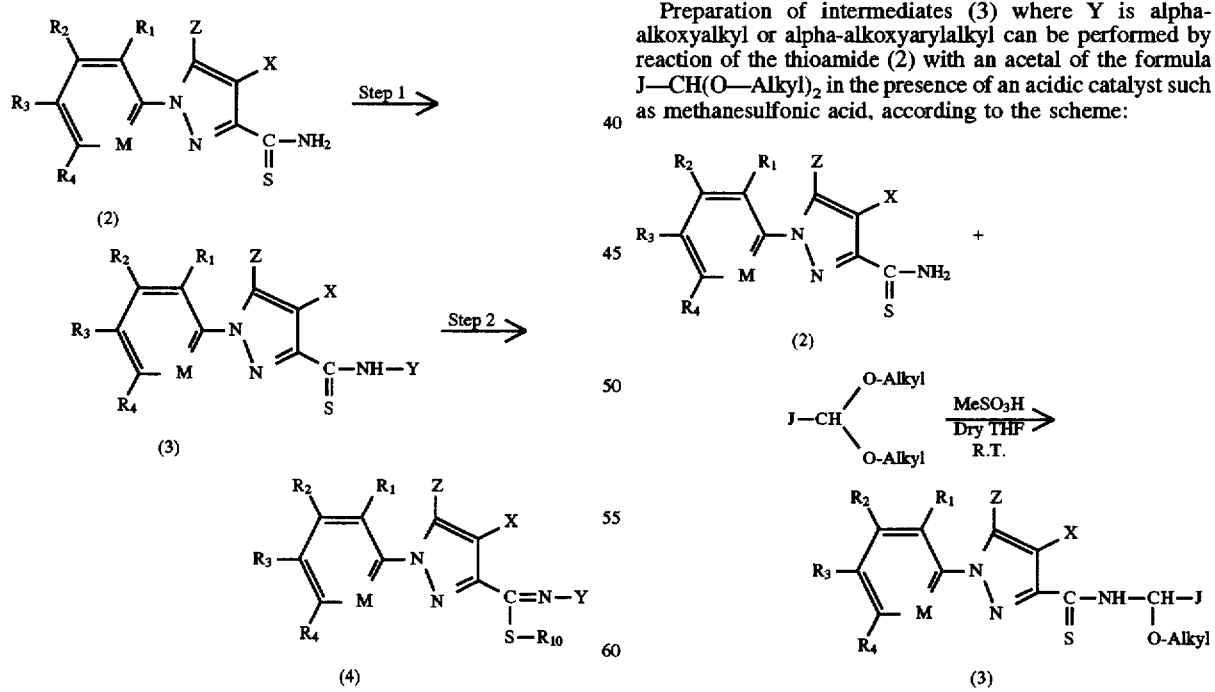

Step 1: Preparation of (3)

Preparation of intermediates (3) where Y is alkyl, arylalkyl, alkenyl or alkynyl can be performed by reaction of the thioamide (2) with an aldehyde J—CHO and benzotriazole (5), under dehydrating conditions, followed by sodium borohydride reduction of intermediate (6) to give (3), as follows:

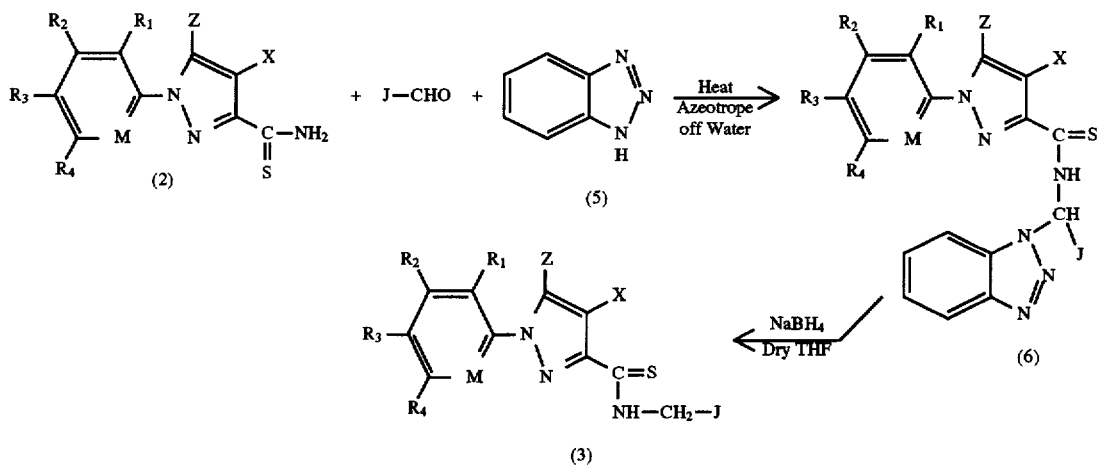

The carbon chain length of J is selected to be one less than that of the radical Y so that Y is J—$CH_2$—. The first, condensation step is conducted in a refluxing solvent such as benzene, toluene, chlorobenzene or xylenes with azeotropic removal of by-product water. Reduction of (6) to (3) is performed with a borohydride, such as sodium or lithium borohydride, in a dry solvent such as anhydrous tetrahydrofuran, dioxane or ethyl ether. The reduction is conducted at temperatures of from about room temperature to about 100° C., with from about 50° C. to about 70° C. being preferred. This procedure is described in *Tetrahedron Letters* 29 (15), pp. 1755-1758 (1988).

Preparation of intermediates (3) where Y is alpha-alkoxyalkyl or alpha-alkoxyarylalkyl can be performed by reaction of the thioamide (2) with an acetal of the formula J—CH(O—Alkyl)$_2$ in the presence of an acidic catalyst such as methanesulfonic acid, according to the scheme:

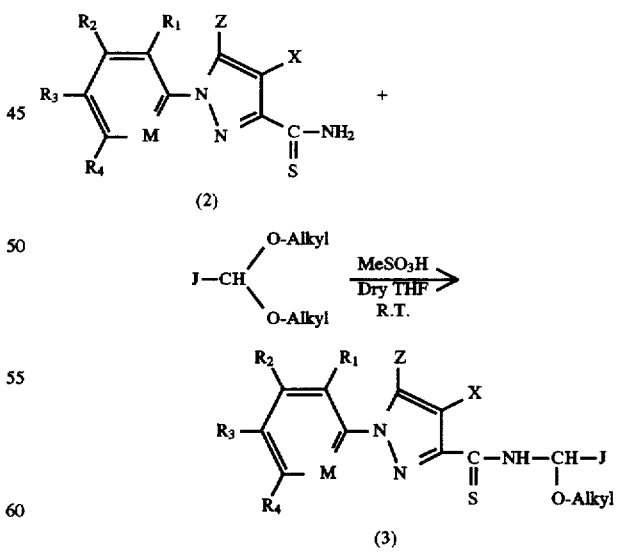

In the above procedure, J is alkyl or aryl and —O—Alkyl refers to lower alkoxy (preferably methyl or ethyl). The reaction is conducted in a solvent such as anhydrous tetrahydrofuran (THF), ethyl ether, dioxane or benzene. Tetrahydrofuran is preferred.

Room temperature is preferred for the reaction, but temperatures of from about 0° C. to about 100° C. are operable. The acid catalyst can be dry toluenesulfonic acid, boron trifluoride or methanesulfonic acid, the latter being preferred. This method is described in *Synthesis* (1977), pp. 250–252.

Preparation of intermediates (3) in which Y is alkylcarbonyl, aroyl or arylalkylcarbonyl can be conducted by reaction of the thioamide (2) with an appropriate acid halide Y-halogen or acid anhydride Y—O—Y. Examples of suitable acid halides are acetyl chloride and benzoyl chloride. 2-Chloropropionic anhydride and 4-chlorophenylacetic anhydride typify suitable anhydrides. The reaction is as follows, in which Y is J—C(=O)—:

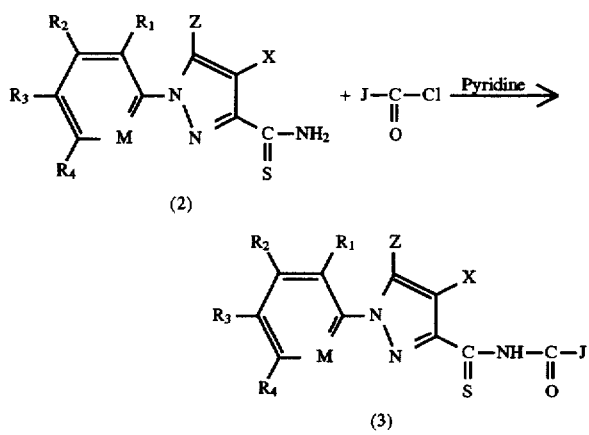

The reaction can be conducted in a solvent such as dry acetone, benzene, toluene or chloroform and at temperatures of from about –40° C. to about 100° C. An acid acceptor, such as pyridine or triethylamine, can be employed, particularly when operating at temperatures of from about 0° C. to about room temperature, or the reaction can be made to proceed by heating in the absence of an acid acceptor. Reactions of this type are described in *Chem. Ber.*, 93, pp. 663–670 (1960).

In Formula (I), compounds having the desired Z substituent are prepared from the corresponding nitriles (A) or (B), having the same Z substituent, and these precursor nitriles are then convened to the thioimidates (I), as the final step, according to the procedures described above. The following directions apply to the preparation of the correctly substituted nitrile precursors, (A) or (B).

In Formulas (A) and (B), precursor nitriles with the substituent Z being H, halogen, alkyl, cyano, nitro, trialkylsilyl, trialkylsilylmethyl, amino or $R_{14}S(O)_n$—, as well as Z being $R_7NH$— and/or $R_8R_9N$— with $R_7$, $R_8$ and $R_9$ being lower alkyl, formyl, alkylcarbonyl, alkoxycarbonyl and alkylthio, can be prepared according to the methods described in WO 87/03781.

Compounds of Formulas (A) and (B) in which the substituent Z is formyl, alkylcarbonyl, haloalkylcarbonyl, haloalkyl, hydroxyalkyl, alkoxyalkyl, cyanoalkyl, alkoxyalkylcarbonyl, $R_{16}S(O)_n$—, alkenyl, alkynyl, alkoxycarbonyl or alkylthiocarbonyl can be prepared according to the procedures described in copending U.S. patent application Ser. No. 08/357,569 filed Dec. 16, 1994, incorporated by reference herein.

Formula (A) and (B) compounds in which the substituent Z is hydrazino, azido, 1H-pyrrol-1-yl or 1H-pyrazol-1-yl can be prepared according to the procedures described in EP 0352944.

Compounds of Formulas (A) and (B) wherein the substituent Z is $R_7NH$— or $R_8R_9N$—, in which $R_7$, $R_8$ and $R_9$ are lower alkyl, which is further substituted with the group $R_{17}$, in which $R_{17}$ is cyano, nitro, alkoxy, $R_{16}S(O)_n$—, alkylcarbonyl, alkoxycarbonyl, aminocarbonyl, alkylaminocarbonyl, dialkylaminocarbonyl, halogen or hydroxy, can be prepared according to the methods described in copending U.S. patent application Ser. No. 08/317,502, filed Oct. 4, 1994, incorporated by reference herein. Preparation of compounds in which $R_{17}$ is cyano or aminocarbonyl is also described in copending U.S. patent application Ser. No. 08/317,976, filed Oct. 4, 1994, incorporated by reference herein.

Compounds of Formulas (A) and (B) wherein the substituent Z is $R_{14}S(O)_n$—, in which $R_{14}$ is alkenyl or alkynyl, optionally substituted with halogen, can be prepared according to the methods described in EP 0403309.

Compounds of Formulas (A) and (B) wherein the substituent Z is alkoxy can be prepared according to the procedures described in U.S. Pat. No. 5,079,370. Compounds in which Z is aryl—$S(O)_n$— or arylalkyl—$S(O)_n$— can be prepared according to the procedures described in EP 0403300.

In Formulas (A) and (B), compounds wherein the substituent Z is $R_7NH$— or $R_8R_9N$—, in which $R_7$–$R_9$ is alkenyl or alkynyl can be prepared according to the general directions given in the alkylation procedure of Method II of the above-referenced copending U.S. patent application Ser. No. 08/317,502, except that alkenyl halides or alkynyl halides, respectively, are used in place of alkyl halides. Examples of alkenyl halides are allyl chloride and 1-bromo-3-butene. Alkynyl halides are exemplified by propargyl bromide and 1-chloro-5-methoxy-3-pentyne. The reaction conditions for preparing the N-alkenyl and N-alkynyl compounds are the same as for the alkyl-substituted compounds.

In Formulas (A) and (B), compounds in which the substituent Z is $R_7NH$— or $R_8R_9N$—, in which $R_7$–$R_9$ is alkylthiocarbonyl, can be synthesized according to the procedure described in WO 87/03781 for the preparation of compounds in which $R_7$, $R_8$ and/or $R_9$ are alkylcarbonyl groups, but employing alkyl chlorothiolformate esters (e.g., ethyl chlorothiolformate) in place of acyl halides. In the same manner, compounds in which $R_7$–$R_9$ is aroyl can be made by the same procedure, using aroyl halides or aroyl anhydrides (e.g., benzoyl chloride, 3-chlorobenzoic anhydride) in place of acyl halides.

In Formulas (A) and (B), compounds (III) wherein the substituent Z is $R_7NH$— or $R_8R_9N$—, wherein $R_7$–$R_9$ is —P(=O)($R_5$)($OR_5$), can be prepared by reacting (A) or (B) with an alkylphosphonochloridic acid ester (II) in the presence of an acid acceptor, according to the scheme:

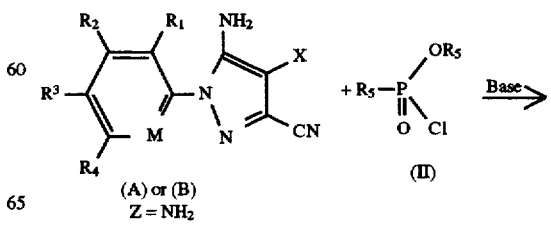

-continued

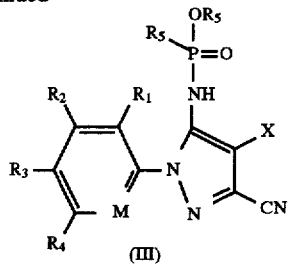

The reaction can be conducted in a solvent such as tetrahydrofuran or N,N-dimethylformamide, and a base such as triethylamine or pyridine can be used as the acid acceptor. Temperatures of from about 15° C. to about 30° C. are preferred but can range from about −50° C. to about 80° C. As an alternate method, a salt of (A) or (B), such as a sodium salt, can first be prepared by reacting (A) or (B) with a metal hydride, such as sodium or potassium hydride, in a solvent such as N,N-dimethylformamide, followed by addition of the phosphonochloridic ester (II). The alkylphosphonochloridic esters can be prepared by the procedure of *Synthetic Communications* 18 (3), 285–9 (1988) involving the reaction of a dialkyl phosphonate (IV) with triphenylphosphine dichloride (V), according to the scheme:

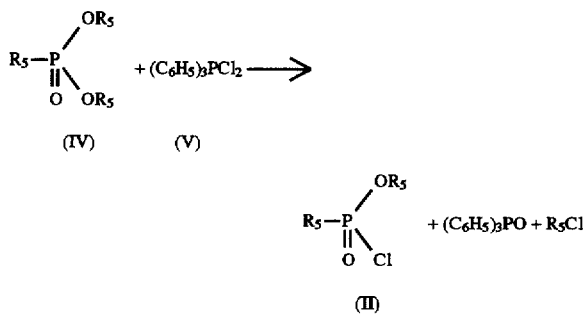

The reaction is best conducted at room temperature, although temperatures from about −50° C. to about 100° C. can be employed. Chloroform is the preferred solvent; however, dichloromethane and toluene are acceptable alternatives.

In Formulas (A) and (B), compounds wherein the substituent Z is $R_7NH$— and/or $R_8R_9N$—, in which $R_7$–$R_9$ is lower alkyl—$S(O)_n$— with n being 1 or 2, can be prepared from compounds in which $R_7$–$R_9$ is lower alkyl—S— by oxidation with 3-chloroperbenzoic acid as described in *Synthesis* (1977), page 798. The reaction can be conducted in a solvent such as a hydrocarbon, chloroform or ethyl acetate, at temperatures from about 0° C. to about 100° C., hexane being the preferred solvent. Other oxidants which can be used include hydrogen peroxide, peroxytrifluoroacetic acid and potassium permanganate.

Other Formula (A) and (B) compounds, wherein the substituent Z is $R_7NH$— or $R_8R_9N$—, in which $R_7$–$R_9$ is a radical containing an alkyl moiety, which alkyl moiety is further substituted by $R_{15}$, can be prepared according to the alkylation procedure of Method II of the above referenced copending U.S. patent application Ser. No. 08/317,502 by employing the appropriately substituted alkyl halide or alkyl sulfate. Thus, for example, substituted alkyl halides wherein $R_{15}$ is haloalkoxy, hydroxycarbonyl, aminosulfonyl, alkylaminosulfonyl or dialkylaminosulfonyl can be made to react with (A) or (B), in which Z is $NH_2$, under conditions similar to those for the above-described compounds.

In Formulas (A) and (B), compounds wherein the substituent Z is alkylcarbonylthio, alkoxycarbonylthio or aroylthio can be prepared by a three-step sequence beginning with the corresponding pyrazoles in which Z is halogen (described in WO 87/03781). This is illustrated in the the scheme below in which the precursor in which Z is halogen is represented by PYRZ—Br, defined as follows:

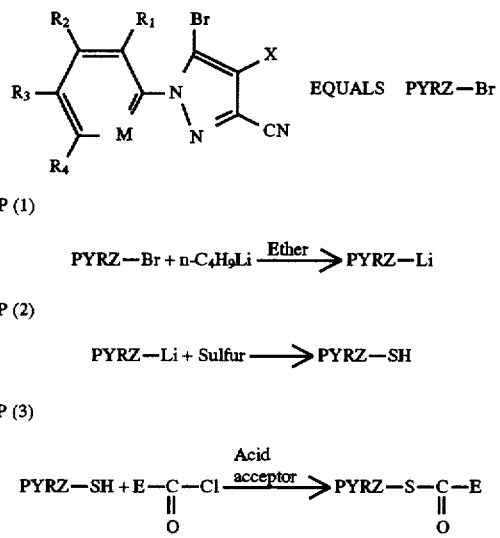

wherein E is alkyl, alkoxy or aryl. In the above scheme, Step (1) is conducted by addition of the organolithium reagent to the 5-bromopyrazole in an inert solvent such as anhydrous ether or tetrahydrofuran at a temperature of from about −50° C. to about −90° C., a temperature of about −78° C. being preferred and the reaction being stirred for about two hours as described in German Patent DE 3711928.

In Step (2), powdered sulfur is added slowly to the reaction mixture, with stirring until completion of the reaction, at which point the mixture is hydrolyzed with dilute hydrochloric acid and worked up, as described in *Jour. Amer. Chem. Soc.*, 71, 1478 (1949). Step (3) entails acylation of the thiol with an acyl, aroyl or alkoxycarbonyl halide. This is best accomplished in a solvent such as tetrahydrofuran, dioxane or benzene in the presence of an acid acceptor such as triethylamine. The procedure is essentially the same as described for the procedure described in WO 87/03781 for preparation of compounds in which $R_7$–$R_9$ is alkylcarbonyl.

In Formulas (A) and (B), compounds in which Z is $R_{15}CO$—, in which $R_{15}$ is an alkyl group substituted by hydroxy, can be prepared by alkaline hydrolysis of the corresponding compounds in which $R_{15}$ is an alkyl group substituted by a halogen, such as chlorine. Such a hydrolysis can be performed by heating with an aqueous solution of sodium bicarbonate at a temperature of about 150° C. for approximately five hours in an autoclave. This procedure is described in *Bull Soc. Chim. France*, (1950), p. 845.

In Formulas (A) and (B), Compounds in which Z is —CH=NOH or —CH=NO—alkyl are prepared by reacting the coresponding compounds in which Z is formyl, described in the above-referenced copending U.S. patent application Ser. No. 08/357,569 filed Dec. 16, 1994, with hydroxylamine and/or an O-alkylhydroxylamine, respectively. Hydroxylamine hydrochloride or sulfate is usually reacted with the formyl compound in the presence of an acid acceptor such as sodium carbonate, pyridine or triethylamine in solution in a solvent such as ethanol, methanol, water, an aqueous alcohol or tetrahydrofuran. Depending upon the reactivity of the formyl derivative, the reaction proceeds at room temperature or requires refluxing of the mixture. The temperature range of from about 20° C. to about 100° C. is most frequently employed. Compounds in which Z is —CH=NO—alkyl are prepared by the same procedure, simply replacing the hydroxylamine salt with the correct O—alkylhydroxylamine salt. The procedure described in *Organic Synthesis Collective*, Vol. II, pp. 313–315 is typical.

Illustrative specific compounds of the invention are set forth in Table 1 below.

said locus an arthropodicidally or nematocidally effective amount of a compound of formula (I) or a composition comprising said compound and an agriculturally acceptable inert carrier therefor. In a preferred embodiment, the arthropods whose control is desired are insects, and to that end the invention provides a method for controlling insects at a locus comprising applying to said locus an insecticidally effective mount of a compound of formula (I), or an insecticidally effective mount of an insecticidal composition comprising an insecticidally effective mount of a compound of formula (I) and an agriculturally acceptable inert carrier therefor. In another preferred embodiment, control of nema-

TABLE 1

Representative 1-Arylpyrazole-3-thiocarboxamide Derivative Compounds

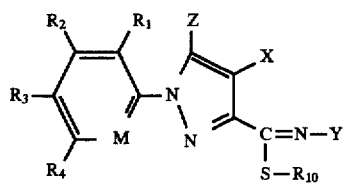

(I)

| No. | Y | $R_{10}$ | X | Z | $R_1$ | $R_2$ | $R_3$ | $R_4$ | M |
|---|---|---|---|---|---|---|---|---|---|
| 1 | H | $CH_3$ | $SOCH_3$ | $NH_2$ | Cl | H | $CF_3$ | H | CCl |
| 2 | H | $C_2H_5$ | $SCF_3$ | $NH_2$ | Br | H | $CF_3$ | H | CCl |
| 3 | H | Allyl | $SO_2CF_3$ | $NHCOCH_3$ | Cl | H | $CF_3$ | H | CF |
| 4 | H | Propargyl | $SO_2CH_3$ | $NH_2$ | Cl | H | $CF_3O$ | H | CCl |
| 5 | H | $CH_3OCH_2$ | SO-cyclopropyl | $NHC_2H_5$ | Cl | H | $CF_3$ | H | CCl |
| 6 | H | $CH_2CH_2CN$ | $SOC_2H_5$ | $NHCH_3$ | F | H | $CF_3$ | $CH_3$ | CCl |
| 7 | H | $CH_2CH_2SO_2CH_3$ | SO-cyclopropyl | $NHCH_2OCH_3$ | Br | H | $CF_3$ | H | CCl |
| 8 | H | $CH_2COOH$ | $SOCH_3$ | $NHCH_2CONH_2$ | Cl | H | $CF_3$ | H | N |
| 9 | H | $CH_3SCH_2$ | $SCF_2Br$ | $NH_2$ | Cl | H | $CF_3O$ | H | CCl |
| 10 | H | $CH_2CO_2CH_3$ | $CF_3$ | NHCHO | Cl | $CH_3$ | $CF_3S$ | H | CBr |
| 11 | H | $(CH_3)_2NCH_2$ | $SCH_3$ | $NH_2$ | Cl | H | $CF_3$ | $CH_3$ | CF |
| 12 | $CH_3$ | $CH(CH_3)CH=CH_2$ | $SOCH_3$ | $NHSO_2C_2H_5$ | Cl | H | $CHF_2$ | H | CCl |
| 13 | Propargyl | $n-C_4H_9$ | SO-i-Pr | Br | F | H | $CClF_2$ | H | CF |
| 14 | $CH_3CO$ | $CH_3$ | $C_2F_5$ | H | Cl | H | $CF_3$ | H | CBr |
| 15 | $ClCH_2CH_2$ | $O_2NCH_2CH_2$ | $C_2H_5SO$ | $CH_3$ | Cl | H | $CF_3O$ | H | CCl |
| 16 | $CH_3CH(OMe)$ | 3-Chloro-Ph | $SO_2CF_3$ | $OCH_3$ | Br | $CH_3$ | $CF_3$ | H | CCl |
| 17 | $i-C_3H_7$ | $CH_2CN$ | $SOCH_3$ | $NH_2$ | Cl | H | $CF_3$ | H | $CCH_3$ |
| 18 | $CH_2CH=CH_2$ | $n-C_6H_{13}$ | $SCH_3$ | $NH_2$ | Cl | H | $CF_3$ | H | CCl |
| 19 | $CH_2CH_2CN$ | $CH_3CONHCH_2$ | $SOCH_3$ | $NHCH_2CH_2CN$ | Cl | H | $CF_3$ | H | CCl |
| 20 | $C_6H_5CO$ | $i-C_3H_7$ | $SO_2CH_3$ | $NHCH_2CH_2OCH_3$ | Cl | H | $CF_3$ | $CH_3$ | CCl |
| 21 | $C_6H_5CH(OEt)$ | 4-Pyridinyl | $SOCF_3$ | $NH_2$ | Cl | H | $CF_3$ | H | N |
| 22 | —$CH_2$——$CH_2$— | | $SCFClBr$ | $N_3$ | Br | H | $CF_3O$ | H | CCl |
| 23 | $n-C_4H_9CO$ | $CH_3$ | $SCH=CH_2$ | $NHCH_3$ | Cl | H | $CF_3$ | H | CCl |
| 24 | $C_4H_9OCO$ | Phenyl | $SOCH_3$ | $NH_2$ | Br | H | $CF_3$ | H | N |
| 25 | $CH_3OCO$ | $i-C_3H_7$ | $SCF_3$ | $NH_2$ | Cl | H | $CF_3$ | H | CCl |
| 26 | $(CH_3)_3CCO$ | Cyclohexyl | $SOCH_3$ | $CH=CH_2$ | F | $CH_3$ | $CF_3$ | H | CF |
| 27 | H | Benzyl | $SO_2CH_3$ | $NH_2$ | Cl | H | $CF_3$ | H | CCl |
| 28 | —$CH_2$—$CH_2$—$CH_2$— | | $SOCF_3$ | $NHCO_2CH_3$ | Cl | H | $CF_2Cl$ | H | $CNO_2$ |
| 29 | $C_6H_5CH_2$ | $C_2H_5$ | $SCH_3$ | $NHCO_2Ph$ | Cl | H | $CFCl_2$ | H | CCl |
| 30 | $BrCH_2CH_2$ | $CH_3COCH_2$ | $CF_2Cl$ | $NHCH_2CH_2SCH_3$ | F | H | $CF_3$ | H | CCl |
| 31 | $n-C_3H_7$ | $CH_3$ | $SOC_2H_5$ | $CH_3$ | Cl | H | $CF_3$ | H | CCl |
| 32 | $CH_2CH=CH_2$ | 3-Pyridinyl | $SOC_2H_5$ | $CH_3$ | H | H | $CF_3$ | H | CCN |
| 33 | H | $CH_2CONH_2$ | $SOCH_3$ | $CH_3$ | H | H | $CF_3$ | H | CCl |
| 34 | Cyclohexyl | $n-C_5H_{11}$ | $SOC_2H_5$ | $N(CH_3)_2$ | H | H | $CF_3$ | H | CCl |
| 35 | H | $4-CH_3O-Ph$ | $SOCH_3$ | $N(CH_3)_2$ | Cl | H | $CF_3$ | H | CBr |

The present invention provides a method for controlling arthropods or nematodes at a locus comprising applying to todes is desired, and to that end the invention provides a method of controlling nematodes at a locus comprising applying to said locus a nematocidally effective mount of a compound of formula (I), or a nematocidally effective amount of a nematocidal composition comprising a nematocidally effective amount of a compound of formula (I) and an agriculturally acceptable inert carrier therefor. Preferably, the locus to which the arthropodicidally (especially insecticidally) or nematocidally effective mount is applied is a crop-growing area, that is, an area in which a crop is growing or in which a crop has been planted, or an area in which a crop will be planted/grown.

The compositions which can be used in the invention for the arthropodicidal (especially insecticidal) or nematocidal treatment of the invention can comprise from about 0.001 to about 95% of the active ingredient of formula (I). The term "active ingredient of formula (I)" or "active ingredient" as used herein refers to a compound of formula (I) or salt thereof. The expression "compound of formula (I)" is also used herein to mean the compound or its salt.

The diluted liquid formulations, as applied to the locus to be treated or crop, generally comprise from about 0.001 to about 3% of active ingredient of formula (I), preferably from about 0.1 to about 0.5%.

The solid formulations as applied to the locus or crop generally comprise from about 0.1 to about 8% of active ingredient of formula (I), preferably from about 0.5 to about 1.5%.

The concentrated compositions are compositions which are commercialized or transported or stored. For application to plants, they are normally diluted in water and applied in such diluted form. The diluted forms are part of the invention as well as the concentrated forms.

The concentrated formulations generally comprise from about 5 to about 95% of active ingredient of formula (I), preferably from about 10 to about 50%.

The insecticidal compositions of the invention can be applied once, or more than once, throughout the whole insect season. Insecticidal compositions according to the invention are usually applied to the locus to be treated or crop area at a rate of from about 0.04 to about 2 kg/ha of active ingredient, preferably from about 0.1 to about 1 kg/ha.

The concentrated insecticidal compositions according to the invention can be in the form of a solid, e.g., dusts or granules or wettable powders, or, preferably, in the form of a liquid, such as an emulsifiable concentrate or a true solution.

The compositions according to the instant invention generally comprise from about 0.5 to about 95% of active ingredient. The remainder of the composition up to 100% comprises a carrier as well as various additives such as those hereafter indicated.

By "carrier", there is meant herein an organic or inorganic material, which can be natural or synthetic, and which is associated with the active ingredient and which facilitates its application to the locus to be treated or crop. This carrier is thus generally inert and should be agriculturally acceptable, especially on the contemplated or treated locus or crop. The carrier can be solid (clay, silicates, silica, resins, wax, fertilizers, etc.) or liquid (water, alcohols, ketones, oil solvents, saturated or unsaturated hydrocarbons, chlorinated hydrocarbons, liquified petroleum gas, etc.).

Among the many additives, the compositions of the invention can comprise surfactants as well as other ingredients such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments and polymers.

More generally, the compositions of the invention can comprise all kinds of solid or liquid additives which are known in the art of insecticides and insecticidal treatments.

The surfactants can be of the emulsifying or wetting type, ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives such as alkyl taurates; phosphoric esters; or esters of alcohols or polyoxyethylated phenols. When the spraying vehicle is water, the use of at least one surfactant is generally required because the active ingredients are not water-soluble.

The method of application of the compositions of the invention is generally the spraying of a mixture which has been previously made by dilution of more concentrated formulations according to the invention.

Solid compositions can be powders for dusting or for dispersion (wherein the content of active ingredient can be up to 100%) and granules, especially extruded or compacted granules, or granules which have been made by impregnation of a powder (the content of active ingredient in such powders can then be between about 1 and about 80%).

Liquid compositions or compositions which have to be liquid when applied include solutions, water-soluble concentrates, emulsifiable concentrates, emulsions, wettable powders or pastes or water-dispersible granules.

Emulsifiable concentrates generally comprise from about 10 to about 80% of active ingredient; the emulsions when applied generally comprise from about 0.01 to about 20% of active ingredient.

For example, the emulsifiable concentrates can comprise the solvent and, to the extent needed, from about 2 to about 20% of suitable additives as stabilizers, surfactants, penetrating agents, corrosion inhibitors or other additives already recited.

These concentrates are usually diluted in tank water so as to obtain the dilution appropriate for spraying.

The concentrated suspensions can also be applied by spraying and have to be fluid without allowing any solid to separate and fall to the bottom. Generally they comprise from about 1 to about 75% of active ingredient (preferably from about 2 to about 50%), from about 0.5 to about 15% of surfactants, from about 0.1 to about 10% of thickener, and from 0 to about 10% of other suitable additives as already indicated, the remainder being water or an organic liquid wherein the active ingredient is insoluble or has a low solubility.

The wettable powders generally comprise the active ingredient (from about 1 to about 95%, preferably from about 2 to about 80%), the solid carrier, a wetting agent (from 0 to about 5%), a dispersing agent (from about 3 to about 10%) and, to the extent needed, from 0 to about 10% of other additives such as stabilizers and others as already listed.

In order to obtain these wettable powders or dusting powders, it is appropriate to intimately mix the active ingredients and the additives, as by grinding in a mill or similar device.

Dispersible granules are generally made by agglomeration of a powder followed by an appropriate granulation process.

The emulsions herein described can be of the oil-in-water or water-in-oil types. Fluidity of the emulsions can range from low viscosities up to high viscosities approaching those of gels.

Among these many compositions or formulations, one skilled in the art can choose the one most appropriate, according to the specific conditions of the treatment problem.

The compounds and compositions of the invention can also be used in admixtures with another pesticide e.g., an insecticide, acaricide or herbicide.

The invention is illustrated by the following examples which are not considered as limiting the invention but are given to better enable use of it.

EXAMPLE 1

A solution of 0.297 gram (0.00261 mole) of 2-aminoethanethiol hydrochloride in 2.5 milliliters of methanol was added to 1.0 gram (0.00261 mole) of 5-amino-1 -[2,6-dichloro-4-(trifluoromethyl)phenyl]-4-methylsulfinyl-1H-pyrazole-3-carbonitrile, and the mixture was stirred at room temperature for an approximately 17-hour period. The mixture was partitioned between water and dichloromethane and the organic layer was separated, dried over $Na_2SO_4$ and filtered. Solvent was evaporated leaving a residue which was purified by preparative thin-layer chromatography to give 0.186 gram (0.00042 mole) of 5-amino-1-[2,6-dichloro-4-(trifluoromethyl)phenyl]-3-(dihydro-2-thiazolyl)-4-methylsulfinyl-1H-pyrazole having a melting point of 189.5° C. (with decomposition). This compound is referred to hereinafter as Compound 1.

EXAMPLE 2

To a stirred solution of 1.00 gram (0.0024 mole) of 5-amino-1-[2,6-dichloro-4-(trifluoromethyl)phenyl]-4-methylsulfinyl-1H-pyrazole-3-carbothioamide, (Compound 4, prepared as described in applicants' copending U.S. patent application Ser. No. 08/418,680, entitled "PESTICIDAL 1-ARYLPYRAZOLE-3-THIOCARBOXAMIDES", filed concurrently herewith, incorporated by reference herein in its entirety and relied upon) and a few crystals of 18-crown-6 in 30 milliliters of dry tetrahydrofuran, was added 0.27 gram (0.00244 mole) of potassium tertiary-butoxide, and the mixture was stirred for a few minutes. A 0.16 milliliter (0.00264 mole) portion of methyl iodide was then injected into the reaction mixture, followed by stirring for a two-hour period. An additional 0.08 milliliter (0.0013 mole) portion of methyl iodide and 0.09 gram of potassium tertiary-butoxide were added and stirring was continued for a period of 17 minutes. The mixture was neutralized by passing in gaseous $CO_2$ for about 10 minutes and volatiles were then removed under reduced pressure. The residue was taken up in dichloromethane and filtered, and the filtrate was evaporated to give the product as a crude residue. This was chromatographed on silica, eluting with 2:1 ethyl acetate/hexane, followed by a second chromatography employing 4:1 chloroform/acetone as the solvent, resulting in 0.67 gram (0.00155 mole) of 5-amino-1-[2,6-dichloro-4-(trifluoromethyl)phenyl]-4-methylsulfinyl-1H-pyrazole-3-carboximidothioic acid methyl ester (99.2% purity) having a melting point of 206.5° C. This compound is referred to hereinafter as Compound 2.

EXAMPLE 3

In a manner similar to that described in EXAMPLE 2, allyl iodide was reacted with 5-amino-1-[2-bromo-6-chloro-4-(trifluoromethyl)phenyl]-4-methylsulfinyl-1H-pyrazole-3-carbothioamide (Compound 6, prepared as described in applicants' concurrently filed, copending application referenced in EXAMPLE 2 above) to give 5-amino-1-[2-bromo-6-chloro-4-(trifluoromethyl)phenyl]-4-methylsulfinyl-1H-pyrazole-3-carboximidothioic acid 2-propenyl ester having a melting point of about 91° C. This compound is referred to hereinafter as Compound 3.

EXAMPLE 4

In a manner similar to that described in EXAMPLE 2, methyl iodide was reacted with 5-amino-1-[2-bromo-6-chloro-4-(trifluoromethyl)phenyl]-4-methylsulfinyl-1H-pyrazole-3-carbothioamide (Compound 6, prepared as described in applicants' concurrently filed, copending application referenced in EXAMPLE 2 above) to give 5-amino-1-[2-bromo-6-chloro-4-(trifluoromethyl)phenyl]-4-methylsulfinyl-1H-pyrazole-3-carboximidothioic acid methyl ester having a melting point of 203.5° C. This compound is referred to hereinafter as Compound 4.

Biological Efficacy

The following representative methods were used to apply the compounds of the invention and to observe the biological activity obtained therefrom: a soil drench on aphid-infested plants, a foliar/contact spray on sucking (aphids) or chewing (Lepidoptera) insects, a bait test on flies and a soil-drench test on nematodes.

The species tested were as follows:

| GENUS, SPECIES | COMMON NAME | ABBREVIATION |
| --- | --- | --- |
| Aphis gossypii | cotton leaf aphid | APHIG |
| Schizaphis graminum | greenbug | TOXOG |
| Musca domestica | housefly | MUSCDO |
| Meloidogyne incognita | southern root-knot nematode | MELGIN |
| Diabrotica virgifera vergifera | western corn rootworm | WCW |

The Soil Drench Test (Systemic Activity; Aphids and Southern Root-Knot Nematode)

Cotton and sorghum plants were established in pots. One day prior to treatment, each pot was infested with about 25 aphids of a mixed population. Cotton plants were infested with aphids and sorghum plants were infested with the greenbug. The selected compound of formula (I) was applied to the soil surface in a dilution that delivered the equivalent of 10.0 ppm soil concentration by weight. Aphid counts were obtained at 5 DAT (i.e., days after treatment). The number of aphids on the treated plants was compared to the number of those on the untreated control plants. The same method was used for the nematode test.

Western Corn Rootworm Bioassay

Soil was placed in a jar and was treated with the selected compound of formula (I) to obtain a soil concentration of 0.5 ppm. 10 neonate Diabrotica virgifera virgifera (western corn rootworm) and 2 pregerminated corn seeds were placed in the jar. The jars were incubated at optimal conditions in a growth chamber for 6 days. The contents of the jar was then dispensed into a berlese funnel under intense light for two additional days. Live WCW larvae migrated through the soil and were collected in a water jar beneath the funnel. WCW larvae not collected in the water were considered dead from contact or ingestion of compound or treated plant matter in the jar.

The Housefly Bait/Contact Test

About 25 four to six-day-old adult houseflies (Musca domestica) were anesthetized and placed in a cage with a sugar water bait solution containing the compound. The compound concentration in the bait solution was 100 ppm. After 24 hours, flies which showed no movement on stimulation were considered dead.

Foliar/Contact Test with *A. gossypii*

Aphid-infested cotton plants were placed on a revolving turntable, and sprayed to runoff with a 100 ppm formulation of the selected compound of formula (I). The treated *A. gossypii*-infested plants were held for three days after treatment, after which the dead aphids were counted.

TABLE 2

| COMPOUND | SYSTEMIC | | FOLIAR/CONTACT | | SOIL | |
|---|---|---|---|---|---|---|
| | BIOLOGICAL ACTIVITY | | | | | |
| NUMBER | APHIG | TOXOG | MUSCDO | APHIG | WCW | MELGIN |
| 1 | + | + | X | − | + | − |
| 2 | X | X | X | X | − | X |
| 3 | X | X | | | | |
| 4 | X | X | X | X | + | + |

"X" = highly active, "+" = moderately active, "−" = low activity

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound having the formula:

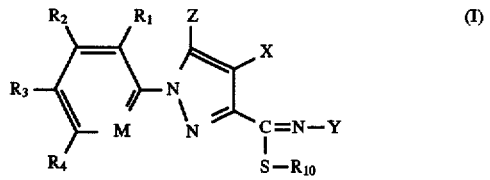

or an agriculturally acceptable salt thereof, wherein:

$R_1$ is H or halogen;
$R_2$ is H, halogen or lower alkyl;
$R_3$ is halogen, haloalkyl, haloalkoxy, $R_{16}S(O)_n$ or $SF_5$;
$R_4$ is H, halogen or lower alkyl;
X is $R_6$ or $—S(O)_n—R_5$;
n is 0, 1 or 2;
$R_5$ is a lower hydrocarbyl or halohydrocarbyl radical which is saturated or is ethylenically or acetylenically unsaturated, or a $C_3$-$C_5$ cycloalkyl radical;
$R_6$ is one of the meanings given for $R_5$, or $R_6$ is thiocyanato, nitro, cyano or halogen;
Z is hydrogen; halogen; a lower alkyl radical which is unsubstituted or is substituted by one or more substituents selected from the group consisting of halogen, hydroxy, alkoxy, alkenyl and cyano; $R_{14}S(O)_n$; $R_{16}S(O)_n$alkyl; amino; $R_{15}CO—$ in which $R_{15}$ is H or an alkyl radical which is unsubstituted or is substituted by one or more halogen, hydroxy or alkoxy; cyano; nitro; trialkylsilyl; trialkylsilylmethyl; alkoxycarbonyl; alkylthiocarbonyl; hydrazino; $—CH=NOH$; $—CH=NO—$alkyl; $C_2$-$C_4$ alkenyl; $C_2$-$C_4$ alkynyl; alkoxy; alkylcarbonylthio; alkoxycarbonylthio; aroylthio; aryl—$S(O)_n$; azido; arylalkyl—$S(O)_n$; 1H-pyrrol-1-yl; 1H-pyrazol-1-yl; $R_7NH—$; or $R_8R_9N—$;

each of $R_7$, $R_8$ and $R_9$, which are identical or different, is lower alkyl, lower alkyl—$S(O)_n$, $P(=O)(R_5)(OR_5)$, aroyl, aryloxycarbonyl, formyl, alkenyl, alkynyl, alkoxycarbonyl, alkylthiocarbonyl or alkylcarbonyl, the alkyl portion of which radicals is unsubstituted or is substituted by one or more $R_{17}$;

or $R_8$ and $R_9$ are joined so as together to form a divalent radical having 4 to 6 atoms in the chain, said divalent radical being alkylene, alkyleneoxyalkylene or alkyleneaminoalkylene;

the groups $S—R_{10}$ and $N—Y$ are joined together, with the $—C=$ group to which they are attached, to form a heterocyclic ring having 5 to 8 ring atoms;

$R_{14}$ is lower alkyl, lower alkenyl or lower alkynyl, optionally substituted with halogen;

$R_{16}$ is lower alkyl or lower haloalkyl;

$R_{17}$ is hydrogen, nitro, cyano, alkoxy, haloalkoxy, $R_{16}S(O)_n$, alkylcarbonyl, alkoxycarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl;

M is C—halo, C—CN, C—$CH_3$, C—$CH_2F$, C—$NO_2$, C—$CH_2Cl$ or N, provided that when $R_1$ is halogen, then M can also be CH.

2. The compound according to claim 1, wherein X is $—S(O)_n—R_5$.

3. The compound according to claim 1, wherein $R_3$ is halogen, haloalkyl or haloalkoxy.

4. The compound according to claim 1, wherein $R_5$ is alkyl, haloalkyl, alkenyl, haloalkenyl, alkynyl or haloalkynyl.

5. The compound according to claim 4, wherein $R_5$ is alkyl.

6. The compound according to claim 1, having the formula:

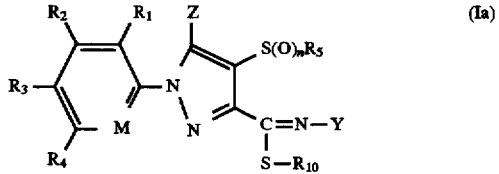

wherein:

M is CH, CCl, CF, CBr or N;
$R_1$ is F, Cl, Br or H, provided that $R_1$ is other than H when M is CH;
$R_2$ and $R_4$ are H;
$R_3$ is $—CF_3$, $—OCF_3$, $—CHF_2$, $—S(O)_nCF_3$, $—CF_2Cl$, $—CFCl_2$, $—OCF_2Cl$, $—OCFCl_2$, Cl, Br or F;

Z is H, F, Cl, Br, $C_1$–$C_3$ alkyl, $C_1$–$C_3$ haloalkyl, $C_2$–$C_3$ alkenyl, alkoxy, alkylthio, alkylsulfinyl, alkylsulfonyl, azido, amino, —$NHR_{11}$ or —$NR_{12}R_{13}$, wherein each of $R_{11}$, $R_{12}$ and $R_{13}$, which are identical or different, is $C_1$–$C_3$ alkyl, $C_2$–$C_3$ alkenyl, $C_1$–$C_5$ alkylcarbonyl or $C_1$–$C_5$ alkoxycarbonyl, in which the alkyl, alkenyl, alkylcarbonyl and alkoxycarbonyl groups are unsubstituted or are substituted by one or more cyano, alkoxy, alkyl—$S(O)_n$—, nitro, alkoxycarbonyl, alkylcarbonyl, aminocarbonyl, alkylaminocarbonyl, dialkylaminocarbonyl, hydroxycarbonyl, hydroxy, F, Cl or Br;

the groups S—$R_{10}$ and N—Y are joined together, with the —C= group to which they are attached, to form a heterocyclic ring having 5 or 6 ring atoms;

and $R_5$, $R_{16}$ and n are as defined in claim 1.

7. The compound according to claim 1, wherein

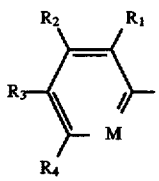

is 2,6-dichloro-4-trifluoromethylphenyl, 2,6-dichloro-4-trifluoromethoxyphenyl, 2-bromo-6-chloro-4-trifluoromethylphenyl, 2-bromo-6-chloro-4-trifluoromethoxyphenyl, 2,6-difluoro-4-trifluoromethylphenyl, 2-chloro-4-trifluoromethylphenyl, 2,6-dichloro-3-methyl-4-trifluoromethylphenyl, 3-chloro-5-trifluoromethyl-2-pyridinyl, 3-chloro-5-trifluoromethoxy-2-pyridinyl, 3,5-dichloro-2-pyridinyl, 2,6-dichloro-4-bromophenyl, 2,4,6-trichlorophenyl, 2-bromo-6-fluoro-4-difluoromethylphenyl, 2-chloro-6-fluoro-4-trifluoromethylphenyl, 2,6-dibromo-4-trifluoromethylphenyl, 2,6-dibromo-4-trifluoromethoxyphenyl or 2-bromo-4-trifluoromethylphenyl.

8. The compound according to claim 1, wherein Z is hydrogen, acetylamino, amino, 2-n-butoxypropionylamino, methyl, hydroxyacetylamino, ethyl, 3-ethylsulfinylpropylamino, bromo, acetyl, formylamino, chloro, methylamino, vinyl, ethylamino, 2-hydroxyethylamino, 2-methoxyethylamino, methylsulfonylamino, 2-ethylsulfonylethylamino, 4-methoxybenzoylamino, 2-cyanoethylamino, 4-methoxybenzylamino, 2-methylthioethylamino, 2-aminocarbonylethylamino, 2-methylsulfinylethylamino, 3-methoxycarbonylpropylamino, 2-ethylsulfinylethylamino, 2-methylsulfonylethylamino, cyanomethylamino, 2-ethylthioethylamino, aminocarbonylmethylamino, dimethylamino, 2-nitroethylamino, 2-acetylethylamino or methylcarbonylmethylamino.

9. The compound according to claim 7, wherein Z is hydrogen, acetylamino, amino, 2-n-butoxypropionylamino, methyl, hydroxyacetylamino, ethyl, 3-ethylsulfinylpropylamino, bromo, acetyl, formylamino, chloro, methylamino, vinyl, ethylamino, 2-hydroxyethylamino, 2-methoxyethylamino, methylsulfonylamino, 2-ethylsulfonylethylamino, 4-methoxybenzoylamino, 2-cyanoethylamino, 4-methoxybenzylamino, 2-methylthioethylamino, 2-aminocarbonylethylamino, 2-methylsulfinylethylamino, 3-methoxycarbonylpropylamino, 2-ethylsulfinylethylamino, 2-methylsulfonylethylamino, cyanomethylamino, 2-ethylthioethylamino, aminocarbonylmethylamino, dimethylamino, 2-nitroethylamino, 2-acetylethylamino or methylcarbonylmethylamino.

10. The compound according to claim 1, wherein —$S(O)_nR_5$ is methylthio, bromodifluoromethylsulfinyl, methylsulfinyl, bromodifluoromethylsulfonyl, methylsulfonyl, difluoromethylthio, trifluoromethylthio, difluoromethylsulfinyl, trifluoromethylsulfinyl, difluoromethylsulfonyl, trifluoromethylsulfonyl, chlorofluoromethylthio, ethylsulfinyl, chlorofluoromethylsulfinyl, ethylsulfonyl, chlorofluoromethylsulfonyl, chlorodifluoromethylthio, bromochlorofluoromethylthio, chlorodifluoromethylsulfinyl, bromochlorofluoromethylsulfinyl, chlorodifluoromethylsulfonyl, bromochlorofluoromethylsulfonyl, dichlorofluoromethylthio, pentafluoroethylthio, dichlorofluoromethylsulfinyl, pentafluoroethylsulfinyl, dichlorofluoromethylsulfonyl, pentafluoroethylsulfonyl, bromodifluoromethylthio, ethylthio, vinylthio, vinylsulfinyl, cyclopropylthio, cyclopropylsulfinyl, cyclopropylsulfonyl, isopropylsulfinyl, isopropylsulfonyl or isopropylthio.

11. The compound according to claim 7, wherein —$S(O)_nR_5$ is methylthio, bromodifluoromethylsulfinyl, methylsulfinyl, bromodifluoromethylsulfonyl, methylsulfonyl, difluoromethylthio, trifluoromethylthio, difluoromethylsulfinyl, trifluoromethylsulfinyl, difluoromethylsulfonyl, trifluoromethylsulfonyl, chlorofluoromethylthio, ethylsulfinyl, chlorofluoromethylsulfinyl, ethylsulfonyl, chlorofluoromethylsulfonyl, chlorodifluoromethylthio, bromochlorofluoromethylthio, chlorodifluoromethylsulfinyl, bromochlorofluoromethylsulfinyl, chlorodifluoromethylsulfonyl, bromochlorofluoromethylsulfonyl, dichlorofluoromethylthio, pentafluoroethylthio, dichlorofluoromethylsulfinyl, pentafluoroethylsulfinyl, dichlorofluoromethylsulfonyl, pentafluoroethylsulfonyl, bromodifluoromethylthio, ethylthio, vinylthio, vinylsulfinyl, cyclopropylthio, cyclopropylsulfinyl, cyclopropylsulfonyl, isopropylsulfinyl, isopropylsulfonyl or isopropylthio.

12. The compound according to claim 8, wherein —$S(O)_nR_5$ is methylthio, bromodifluoromethylsulfinyl, methylsulfinyl, bromodifluoromethylsulfonyl, methylsulfonyl, difluoromethylthio, trifluoromethylthio, difluoromethylsulfinyl, trifluoromethylsulfinyl, difluoromethylsulfonyl, trifluoromethylsulfonyl, chlorofluoromethylthio, ethylsulfinyl, chlorofluoromethylsulfinyl, ethylsulfonyl, chlorofluoromethylsulfonyl, chlorodifluoromethylthio, bromochlorofluoromethylthio, chlorodifluoromethylsulfinyl, bromochlorofluoromethylsulfinyl, chlorodifluoromethylsulfonyl, bromochlorofluoromethylsulfonyl, dichlorofluoromethylthio, pentafluoroethylthio, dichlorofluoromethylsulfinyl, pentafluoroethylsulfinyl, dichlorofluoromethylsulfonyl, pentafluoroethylsulfonyl, bromodifluoromethylthio, ethylthio, vinylthio, vinylsulfinyl, cyclopropylthio, cyclopropylsulfinyl, cyclopropylsulfonyl, isopropylsulfinyl, isopropylsulfonyl or isopropylthio.

13. The compound according to claim 9, wherein —$S(O)_nR_5$ is methylthio, bromodifluoromethylsulfinyl, methylsulfinyl, bromodifluoromethylsulfonyl, methylsulfonyl, difluoromethylthio, trifluoromethylthio, difluoromethylsulfinyl, trifluoromethylsulfinyl, difluoromethylsulfonyl, trifluoromethylsulfonyl, chlorofluoromethylthio, ethylsulfinyl, chlorofluoromethylsulfinyl, ethylsulfonyl, chlorofluoromethylsulfonyl, chlorodifluoromethylthio, bromochlorofluoromethylthio, chlorodifluoromethylsulfinyl, bromochlorofluoromethylsulfinyl, chlorodifluoromethylsulfonyl, bromochlorofluoromethylsulfonyl, dichlorofluoromethylthio, pentafluoroethylthio, dichlorofluoromethylsulfinyl, pentafluoroethylsulfinyl, dichlorofluoromethylsulfonyl, pentafluoroethylsulfonyl, bromodifluoromethylthio, ethylthio, vinylthio, vinylsulfinyl, cyclopropylthio, cyclopropylsulfinyl, cyclopropylsulfonyl, isopropylsulfinyl, isopropylsulfonyl or isopropylthio.

14. The compound according to claim 1, wherein —S—$R_{10}$ and Y—N=C— are joined together to form the divalent radical —S—$CH_2CH_2$—N=C— or —S—$CH_2CH_2CH_2$—N=C—.

15. The compound according to claim 7, wherein —S—$R_{10}$ and Y—N=C— are joined together to form the divalent radical —S—$CH_2CH_2$—N=C— or —S—$CH_2CH_2CH_2$—N=C—.

16. The compound according to claim 8, wherein —S—$R_{10}$ and Y—N=C— are joined together to form the divalent radical —S—$CH_2CH_2$—N=C— or —S—$CH_2CH_2CH_2$—N=C—.

17. The compound according to claim 10, wherein —S—$R_{10}$ and Y—N=C— are joined together to form the divalent radical —S—$CH_2CH_2$—N=C— or —S—$CH_2CH_2CH_2$—N=C—.

18. The compound according to claim 1, which is:

5-amino-1-[2,6-dichloro-4-(trifluoromethyl)phenyl]-3-(dihydro-2-thiazolyl)-4-methylsulfinyl-1H-pyrazole.

19. An arthropodicidal or nematocidal Composition comprising an arthropodicidally or nematocidally effective amount of a compound of formula (I) according to claim 1 or an agriculturally acceptable salt thereof, and an agriculturally acceptable inert carrier therefor.

20. An insecticidal composition comprising an insecticidally effective amount of a compound of formula (I) according to claim 1 or an agriculturally acceptable salt thereof, and an agriculturally acceptable inert carrier therefor.

21. The insecticidal composition according to claim 20, comprising from about 0.001 to about 3% of compound of formula (I) or agriculturally acceptable salt thereof.

22. The insecticidal composition according to claim 21, comprising from about 0.1 to about 0.5% of compound of formula (I) or agriculturally acceptable salt thereof.

23. The insecticidal composition according to claim 20, comprising from about 0.1 to about 8% of compound of formula (I) or agriculturally acceptable salt thereof, said composition being in solid form.

24. The insecticidal composition according to claim 23, comprising from about 0.5 to about 1.5% of compound of formula (I) or agriculturally acceptable salt thereof.

25. A method for controlling arthropods or nematodes at a locus comprising applying to said locus an arthropodicidally or nematocidally effective amount of a compound of formula (I) according to claim 1 or agriculturally acceptable salt thereof.

26. The method according to claim 25, wherein said arthropods are insects and wherein an insecticidally effective amount of said compound or salt is applied to said locus.

27. The method according to claim 25, wherein said locus is a crop area.

28. The method according to claim 25, wherein said compound or salt is applied to said locus at a rate of from about 0.04 to about 2 kg/ha.

29. The method according to claim 28, wherein said compound or salt is applied to said locus at a rate of from about 0.1 to about 1 kg/ha.

* * * * *